United States Patent
Wahl et al.

(10) Patent No.: US 6,379,529 B1
(45) Date of Patent: Apr. 30, 2002

(54) SENSOR ELEMENT DESIGN FOR DETERMINING THE CONCENTRATION OF OXIDIZABLE CONSTITUENTS IN A GAS MIXTURE

(75) Inventors: Thomas Wahl, Pforzheim; Thomas Brinz, Sindelfingen; Bernd Schumann, Rutesheim, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/284,358
(22) PCT Filed: Aug. 7, 1998
(86) PCT No.: PCT/DE98/02266
  § 371 Date: Jul. 20, 1999
  § 102(e) Date: Jul. 20, 1999
(87) PCT Pub. No.: WO99/08101
  PCT Pub. Date: Feb. 18, 1999

(30) Foreign Application Priority Data

Aug. 12, 1997 (DE) .......................... 197 34 861

(51) Int. Cl.⁷ ............................................ G01N 27/407
(52) U.S. Cl. .................... 205/780.5; 205/787; 204/424; 204/426
(58) Field of Search ................ 204/424–429; 205/780.5, 787

(56) References Cited

U.S. PATENT DOCUMENTS

| | | | | |
|---|---|---|---|---|
| 4,225,634 A | * | 9/1980 | Tanaka et al. | 204/429 |
| 4,226,692 A | * | 10/1980 | Isenberg | 204/198 |
| 4,985,126 A | * | 1/1991 | Haefele et al. | 204/406 |
| 5,037,525 A | * | 8/1991 | Badwal | 204/421 |
| 5,520,789 A | * | 5/1996 | Takahashi et al. | 204/424 |
| 6,019,881 A | * | 2/2000 | Kurosawa et al. | 204/424 |

FOREIGN PATENT DOCUMENTS

WO  96/28722  * 9/1996

OTHER PUBLICATIONS

Demitras et al., Inorganic Chemistry, ISBN:0134663694, pp. 208–210, Month unknown 1972.*

Phillips et al., Inorganic Chemistry II Metals, pp. 166–184, Month unknown 1966.*

Murphy et al., Foundations of College Chemistry, 2nd Edition, p. 90, Month unknown 1972.*

* cited by examiner

Primary Examiner—Robert J. Warden, Sr.
Assistant Examiner—Kaj K. Olsen
(74) Attorney, Agent, or Firm—Kenyon & Kenyon

(57) ABSTRACT

The invention proposes a sensing element which serves to determine the concentration of oxidizable constituents in a gas mixture, in particular of hydrocarbons, NO, and $NH_3$. Electrically conductive spinels of the general formula $ABB'O_4$, or electrically conductive pseudobrookites of the general formula $ABB'O_5$, serve in this context as the material for the measurement electrode.

19 Claims, 1 Drawing Sheet

SENSOR ELEMENT DESIGN FOR DETERMINING THE CONCENTRATION OF OXIDIZABLE CONSTITUENTS IN A GAS MIXTURE

BACKGROUND INFORMATION

The present invention is based on a sensing element for determining the concentration of oxidizable constituents in a gas mixture, in particular for the determination of saturated and unsaturated hydrocarbons, nitrogen oxides, and ammonia.

Sensing elements which contain sensor materials of the general formula $A_{2-x}A'_xBO_4$ are known from German Patent 23 34 044 C3. These are rare-earth compounds of the $K_2MgF_4$ structural type, for the detection of oxidizable gases. It is also known from German Patent 42 44 723 A1 to use rare-earth cuprates of the formula $A_{2-x}L_xCuO_4$ for the detection of oxygen in gas mixtures, in particular in exhaust gases of internal combustion engines and combustion facilities. In addition, the article by H. Meixner and U. Lampe in Sensors and Actuators B 1996, 33, pp. 198–202 describes a plurality of metal oxides for the determination of various gas components. For some time, however, it has proven difficult to find suitable materials with high selectivities for, e.g., the determination of saturated and unsaturated hydrocarbons and of ammonia or nitrogen oxides. This was attributable, among other factors, to the poor corrosion stability of the electrode materials used, which often have a strong tendency toward undesirable sulfate formation on the electrode surface.

SUMMARY OF THE INVENTION

In contrast to the known existing art, the sensing element according to the present invention having the material used for the measurement electrode, which contains either an electrically conductive spinel of the general formula $ABB'O_4$ or an electrically conductive pseudobrookite of the general formula $ABB'O_5$, exhibits excellent corrosion resistance at high temperatures, a low tendency to form sulfates, and a high selectivity for oxidizable gaseous compounds. It is thus possible, in a simple and advantageous manner, to determine corrosive ammonia without having the measurement electrode chemically attacked. As a result of the possible structural variations of these two classes of compounds, i.e. the spinels and the pseudobrookites, it is possible to make available a variety of structures for the determination of various gases. Because of their structure, spinels possess a particularly high degree of spatial occupancy, in which one-eighth of the tetrahedral vacancies and half the octahedral vacancies of the oxygen sublattice, which forms approximately a cubic close-packed (ccp) configuration, are occupied by cations. This dense structure, which is also exhibited by the pseudobrookites, inhibits or prevents any diffusion of the metal cations which contaminate the electrode material, derived for example from oxides of exhaust systems, into the metal oxide electrode; this would be associated with poisoning of the electrode and thus with a change in signal.

The features set forth in the dependent claims make possible advantageous developments of and improvements to the sensing element recited in the principal claim.

In a preferred embodiment, what is used as the spinel is a so-called 2,3 spinel, A representing a divalent transition metal cation and B and B' a trivalent transition metal cation. A can, for example, represent the divalent cations of cobalt, nickel, or copper, B the trivalent cations of chromium, iron, and manganese, and B' the trivalent cations of chromium and manganese. 2,3 spinels, for example $NiFeMnO_4$ or $CoCr_2O_4$ or $CoCrMnO_4$, have a high sensitivity in particular for unsaturated hydrocarbons. The oxygen content of the gas mixture, as long as it exceeds 1% in, for example, exhaust gases of internal combustion engines, has no great effect on the selectivity or sensitivity of the measurement signal; the same is true for other gas constituents. The measurement electrode has a thickness of 5–100 $\mu$m, preferably 20–30 $\mu$m.

In a further advantageous embodiment, what is used as the spinel is a 4,2 spinel, A representing a tetravalent transition metal cation and B and B' a divalent transition metal cation. A can be, for example, a tetravalent cation of titanium or zirconium, but niobium is also possible. B and B' can represent, for example, the divalent cations of cobalt and nickel. One possible combination is, for example, $TiCo_2O_4$, so that particularly high sensitivities for nitrogen oxides can be attained with this metal oxide electrode. The sensitivity of these 4,2 spinels for nitrogen oxides is so high that the other constituents of the exhaust gas exhibit no cross-sensitivities. The oxygen content of the lean exhaust gas also has no great influence on the sensitivity of the sensor signal.

A further advantageous embodiment of the sensing element according to the present invention consists in the use of so-called 6,1 spinels, A representing a hexavalent transition metal cation and B and B' a univalent metal cation. A can be, for example, the hexavalent cation of tungsten, molybdenum, or chromium, and B and B' represent, for example, the univalent cations of the coinage metals and of elements of the first main group, for example gold, silver, copper, potassium, lithium, and sodium. Depending on their composition, 6,1 spinels exhibit high sensitivity for a variety of gases, so that with suitable combinations of 6,1 spinels both hydrocarbons and nitrogen oxides, or also ammonia, can be determined.

In a further preferred embodiment, a pseudobrookite of the formula $ABB'O_5$, composed of metallic transition elements, can be used as the sensor material. In this context A represents a tetravalent transition metal cation, and B and B' a trivalent transition metal cation. In particular A represents, for example, the tetravalent cations of titanium and zirconium, niobium also being possible. B and B' represent the trivalent cations of chromium, iron, and manganese. Pseudobrookites according to the present invention have a high sensitivity for saturated and unsaturated hydrocarbons; once again, no cross-sensitivities to the other constituents in a gas mixture occur. The sensing element is also characterized in that occupancy of the positions B and B' is accomplished stoichiometrically or nonstoichiometrically, and correspond to the general empirical formulas $AB_xB'_{2-x}O_4$ and/or $AB_xB'_{2-x}O_5$, where $0<x<2$.

DETAILED DESCRIPTION

Figure 1:
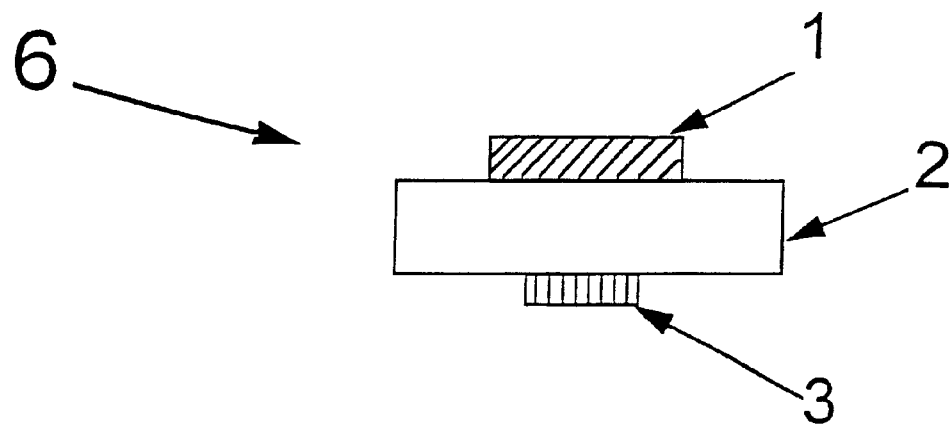
FIG. 1 shows a section through a sensor according to the present invention.

FIG. 1 depicts a sensing element 6 according to the present invention in section. A layer made of a porous or dense solid electrolyte 2, for example comprising yttrium oxide-stabilized zirconium dioxide (YSZ) or other usual solid electrolyte compounds, bears on the one large surface a reference electrode 3 which is made, for example, of platinum or a similar metal, and on the other large surface an electrode 1 which contains a metal oxide according to the present invention. Reference electrode 3 is exposed to the exhaust gas directly, or to the exhaust gas through the porous solid electrolyte or through a lateral diffusion layer or a diffusion layer embedded into the solid electrolyte; this is not depicted in the drawing. Reference electrode 3 can also be exposed to air.

Figure 2:
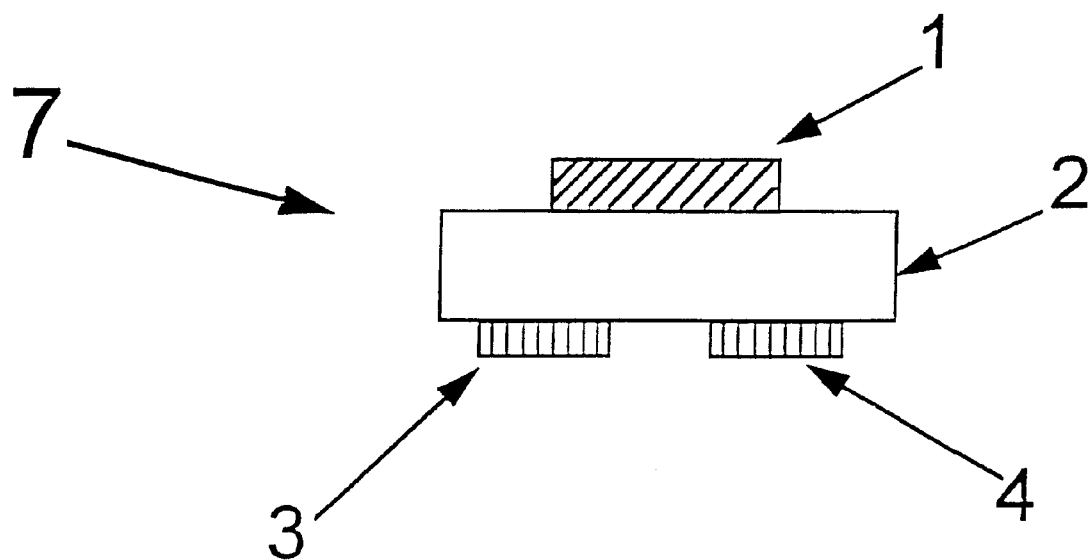
FIG. 2 shows a section through a further sensor according to the present invention.

FIG. 2 shows a further exemplary embodiment of a sensing element 7 according to the present invention, in section. The configuration is identical to the one depicted in FIG. 1, except that a second reference electrode 4 is additionally applied. Here again reference electrodes 3, 4 are exposed to the exhaust gas directly, or to the exhaust gas through the porous solid electrolyte or through a lateral diffusion layer (not depicted) or a diffusion layer embedded into the solid electrolyte. One of the two reference electrodes can also be exposed to air.

Manufacture of the metal oxides according to the present invention, both the spinels and the pseudobrookites, is accomplished using commonly known methods, for example mixing stoichiometric quantities of the corresponding oxides followed by sintering, or using hydrothermal methods.

To determine the concentration of oxidizable constituents in exhaust gases, the sensor is heated by way of a heating apparatus (not depicted in the drawings) to a temperature between 300 and 1000° C., advantageously to approximately 600° C. In order to improve the electrochemical properties, it is furthermore advisable to add some of the spinels or pseudobrookites according to the present invention to the solid electrolyte, in order to increase the reactive surface at the triple-phase boundary.

Hydrocarbons, for example, are electrochemically oxidized on the metal oxide electrode in a manner similar to that in a fuel cell, according to the following semireaction:

$$C_3H_6 + 9O^{2-} \rightarrow 3CO_2 + 3H_2O + 18e^-.$$

The situation is similar for ammonia and nitric oxide, which can be electrochemically oxidized in the presence of oxygen:

$$2NH_3 + 3O^{2-} \rightarrow N_2 + 3H_2O + 6e^-.$$

$$NO + O^{2-} \rightarrow NO_2 + 2e^-.$$

Electrochemical oxidation of the gas constituents takes place in the simultaneous presence of oxygen. The reaction rate necessary for heterogeneous oxidation of hydrocarbons, ammonia, and also nitric oxide at the electrode surface is particularly low in the case of the metal oxides according to the present invention. As a result, hydrocarbons, ammonia, and nitric oxide are effectively oxidized electrochemically in the presence of oxygen, and can be determined separately.

Exemplary embodiments of metal oxide electrodes according to the present invention are set forth in Tables 1 and 2. For example, NiFeMnO, as a representative of the 2,3 spinels, can be used for the determination of hydrocarbons. So can $CoCr_2O_4$ or $CoCrMnO_4$, which have equally good sensitivity for unsaturated hydrocarbons. The high sensitivity of 2,3 spinels in particular for unsaturated hydrocarbons is the result of adsorptive interactions of the π electrons of the double bonds of the corresponding hydrocarbon with electrophilic acceptor locations on the (1,1,0) or (1,1,1) spinel face. Further examples according to the present invention are $MnCr_2O_4$, which can be used for nitrogen oxides.

A 4,2 spinel, for example having the formula $TiCo_2O_4$, possesses outstanding sensitivity for nitric oxide. Pseudobrookites, for example having the formula $TiCr_2O_5$, also have good sensitivity for hydrocarbons and also, in particular, for ammonia.

A manufacturing method for a sensor according to the present invention is described by the example which follows: $NiFeMnO_4$, for example manufactured by mixing the oxides or by hydrothermal synthesis, is printed using a commonly known thick-film technique onto a substrate which bears a reference electrode, made for example of platinum, and above that a solid electrolyte layer comprising, for example, stabilized zirconium dioxide. A heating apparatus is applied on the opposite side of the substrate. The sensor is sintered at 1200° C. for 90 minutes, with a heating/cooling ramp rate of 300° C. per hour. After sintering, the solid electrolyte has pores on the order of 10 μm to 100 μm in size. Once the platinum conductor paths, which contact only the measurement electrode, have been attached and pressed on, the sensor is then ready to operate.

Table 1 shows the correlation between sensor current and $O_2$ concentration. It is clearly evident that the sensitivity of the sensor for unsaturated hydrocarbons is only slightly influenced by the $O_2$ concentration.

Table 2 below lists several examples of a sensor element according to the present invention for determining various gaseous compounds in gas mixtures. The examples serve only for explanation, and do not in any way limit the invention. As is evident from the table, the spinels or pseudobrookites exhibit almost no cross-sensitivity for other gas components in a gas mixture besides the components being determined. It is also evident that the oxygen content of the gas mixture, exemplified by the behavior of $NiFeMnO_4$ in lean exhaust gas, exerts no influence on the signal being measured. This applies to all the spinels and pseudobrookites according to the present invention.

TABLE 1

Influence of $O_2$ concentration on sensitivity and
selectivity of measurement signal for the sensing of
unsaturated hydrocarbons (HC).
$NiFeMnO_4$ measurement electrode
$O_2$-Gehalt.. = $O_2$ concentration (vol %)
Sensorstrom.. = Sensor current (μA) at an HC
concentration of:

| $O_2$ Concentration | Sensor current (μA) at an HC concentration of: | | | | |
|---|---|---|---|---|---|
| (vol %) | 0 ppm | 125 ppm | 250 ppm | 500 ppm | 1000 ppm |
| 0,675 | −0,35 | 3,5 | 7,9 | 14,7 | 22,75 |
| 1,25 | −0,35 | 3,5 | 7,7 | 14 7 | 24,5 |
| 2,5 | −0,7 | 3,15 | 7,35 | 14,0 | 24,5 |
| 5,0 | −1,05 | 3,15 | 7,0 | 13,3 | 22,75 |
| 10,0 | −1,4 | 2,8 | 6,3 | 12,6 | 22,05 |

TABLE 2

Examples of sensing elements according to the present
invention having a measurement electrode made of spinel and/or
pseudobrookite; operating temperature of the sensing element is
850° C. in each case.

| Measurement | $O_2$ Concentration (vol %) | Sensor current (μA) at a gas concentration of: | | | | |
|---|---|---|---|---|---|---|
| | | 430 ppm $C_3H_6$ | 440 ppm $H_2$ | 440 ppm CO | 900 ppm NO | 200 ppm $NH_3$ |
| $CoCR_2O_4$ | 10 | 2, 3 | 0 | 0 | 0, 2 | 1, 0 |
| $CoCrMnO_4$ | 10 | >31 | 1, 2 | 1, 9 | 1, 6 | 22 |
| $TiCr_2O_5$ | 10 | 1, 9 | 0, 28 | 0, 56 | 0, 4 | 2, 2 |
| $MnCr_2O_4$ | 10 | 0, 5 | 0, 3 | 0, 4 | 1, 4 | 0, 6 |
| $TiCo_2O_4$ | 10 | 1, 5 | 0, 5 | 0, 6 | 3, 0 | 1, 2 |

Meβelektrodenmaterial = Measurement electrode material
O2-Gehalt.. = $O_2$ concentration (vol %)
Sensorstrom.. = Sensor current (μA) at a gas concentration of:

What is claimed is:

1. A sensing element for determining a concentration of oxidizable constituents, comprising an ion-conducting solid electrolyte configured with at least one reference electrode and with at least one measurement electrode, wherein the measurement electrode contains an electrically conductive 4,2 spinel of the general formula ABB'O$_4$, and A represents the tetravalent cation of Zr, and B and B' denote cations of transition metals or cations of metals of the first main group.

2. A sensing element for determining a concentration of oxidizable constituents, comprising an ion-conducting solid electrolyte configured with at least one reference electrode and with at least one measurement electrode, wherein the measurement electrode contains an electrically conductive spinel of the general formula ABB'O$_4$ or an electrically conductive pseudobrookite of the general formula ABB'O$_5$, where A, B, and B' denote cations of transition metals or cations of metals of the first main group and the spinel ABB'O$_4$ is a 6,1 spinel, A representing a hexavalent transition metal cation and B and B' a univalent metal cation.

3. The sensing element as defined in claim 2, wherein A represents the hexavalent cations of W or Mo.

4. The sensing element as defined in claim 2, wherein B and B' represent the univalent cations of Au, Ag, Cu, K, or Li.

5. The sensing element as defined in claim 2, wherein the thickness of the measurement electrode is 5 to 100 $\mu$m.

6. The sensing element as defined in claim 2, wherein the thickness of the measurement electrode is 20 to 30 $\mu$m.

7. The sensing element as defined in claim 2, wherein the at least one reference electrode, the oxygen ion-conductive solid electrolyte, and the at least one measurement electrode are arranged in superimposed layers on one surface of a flat, electrically insulating substrate.

8. The sensing element according to claim 2 where the ion conducting solid electrolyte comprises electrically conductive spinels of the same chemical composition as the electrically conductive spinels contained in the measurement electrode.

9. A sensing element for determining a concentration of oxidizable constituents, comprising an ion-conducting solid electrolyte configured with at least one reference electrode and with at least one measurement electrode, wherein the measurement electrode contains an electrically conductive pseudobrookite of the general formula ABB'O$_5$, A representing a tetravalent transition metal cation and B and B' a trivalent transition metal cation.

10. The sensing element as defined in claim 9, wherein A represents the tetravalent cations of Ti or Zr.

11. The sensing element as defined in claim 9, wherein B and B' represent the trivalent cations of Cr, Fe, or Mn.

12. A sensing element for determining a concentration of oxidizable constituents, comprising an ion-conducting solid electrolyte configured with at least one reference electrode and with at least one measurement electrode, wherein the measurement electrode contains an electrically conductive spinel of the general formula AB$_x$B'$_{2-x}$O$_4$, or an electrically conductive pseudobrookite of the general formula AB$_x$B'$_{2-x}$O$_5$, where 0<x <2, x≠1, and A, B, and B' denote cations of transition metals or cations of metals of the first main group, and B and B' are cations of different metals.

13. A sensing element for determining a concentration of oxidizable constituents, comprising an ion-conducting solid electrolyte configured with at least one reference electrode and with at least one measurement electrode, wherein the measurement electrode contains an electrically conductive spinel of the formula NiFeMnO$_4$.

14. A sensing element for determining a concentration of oxidizable constituents, comprising an ion-conducting solid electrolyte configured with at least one reference electrode and with at least one measurement electrode, wherein the measurement electrode contains an electrically conductive spinel of the formula CoCrMnO$_4$.

15. A sensing element for determining a concentration of oxidizable constituents, comprising an ion-conducting solid electrolyte configured with at least one reference electrode and with at least one measurement electrode, wherein the measurement electrode contains an electrically conductive spinel of the formula TiCo$_2$O$_4$.

16. A sensing element for determining a concentration of oxidizable constituents, comprising an ion-conducting solid electrolyte configured with at least one reference electrode and with at least one measurement electrode, where the measurement electrode contains an electrically conductive 2,3 spinel of the general formula ABB'O$_4$, and A represents the divalent cation of Cu, and B and B' denote cations of transition metals or cations of metals of the first main group.

17. A sensing element for determining a concentration of oxidizable constituents, comprising an ion-conducting solid electrolyte configured with at least one reference electrode and with at least one measurement electrode, wherein the measurement electrode contains an electrically conductive pseudobrookite of the general formula ABB'O$_5$, where A, B, and B' denote cations of transition metals or cations of metals of the first main group.

18. A method for determining the concentration of hydrocarbons in a gas, comprising the steps of:

sensing the concentration of hydrocarbons in the gas using an ion-conducting solid electrolyte configured with at least one reference electrode and with at least one measurement electrode, wherein the measurement electrode contains an electrically conductive spinel of the general formula ABB'O$_4$, where A, B, and B' denote cations of transition metals or cations of metals of the first main group, wherein A and B are cations of different metals;

producing an electrical signal indicative of the concentration of hydrocarbons in the gas.

19. A method for determining the concentration of ammonia in a gas, comprising the steps of:

sensing the concentration of ammonia in the gas using an ion-conducting solid electrolyte configured with at least one reference electrode and with at least one measurement electrode, wherein the measurement electrode contains an electrically conductive spinet of the general formula ABB'O$_4$, where A, B, and B' denote cations of transition metals or cations of metals of the first main group, wherein A and B are cations of different metals;

producing an electrical signal indicative of the concentration of ammonia in the gas.

* * * * *